United States Patent
Sagata et al.

(10) Patent No.: US 10,047,317 B2
(45) Date of Patent: *Aug. 14, 2018

(54) FLUOROPOLYETHER COMPOUND, LUBRICANT, MAGNETIC DISK, AND METHOD FOR PRODUCING SAME

(71) Applicant: MORESCO CORPORATION, Kobe-shi, Hyogo (JP)

(72) Inventors: Ryosuke Sagata, Kobe (JP); Tsuyoshi Shimizu, Kobe (JP); Haruo Kasai, Kobe (JP)

(73) Assignee: Moresco Corporation, Kobe-shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/529,841

(22) PCT Filed: Nov. 24, 2015

(86) PCT No.: PCT/JP2015/082882
§ 371 (c)(1),
(2) Date: May 25, 2017

(87) PCT Pub. No.: WO2016/084781
PCT Pub. Date: Jun. 2, 2016

(65) Prior Publication Data
US 2017/0260472 A1   Sep. 14, 2017

(30) Foreign Application Priority Data
Nov. 28, 2014   (JP) .................. 2014-241772

(51) Int. Cl.
| C10M 105/54 | (2006.01) |
| C07C 43/03 | (2006.01) |
| C07C 43/17 | (2006.01) |
| C10M 107/38 | (2006.01) |
| G11B 5/725 | (2006.01) |

(52) U.S. Cl.
CPC ........... *C10M 105/54* (2013.01); *C07C 43/03* (2013.01); *C07C 43/17* (2013.01); *C10M 107/38* (2013.01);
(Continued)

(58) Field of Classification Search
CPC ........ C10N 2240/204; C10M 2213/062; F16C 33/201
(Continued)

(56) References Cited

U.S. PATENT DOCUMENTS 8,679,655 B2   3/2014   Kobayashi
8,980,450 B2   3/2015   Kobayashi
(Continued)

FOREIGN PATENT DOCUMENTS

JP   2006-070173 A   3/2006
JP   2009-211765 A   9/2009
(Continued)

OTHER PUBLICATIONS

International Search Report issued in corresponding International Application No. PCT/JP2015/082882 dated Feb. 3, 2016.
(Continued)

*Primary Examiner* — Vishal Vasisth
(74) *Attorney, Agent, or Firm* — Morgan, Lewis & Bockius LLP

(57) ABSTRACT

Disclosed is a fluoropolyether compound comprising a $C_{4-10}$ aliphatic hydrocarbon chain present in the middle of the fluoropolyether compound and at least two perfluoropolyethers.

17 Claims, 1 Drawing Sheet

(52) U.S. Cl.
CPC ..... *G11B 5/725* (2013.01); *C10M 2211/0425* (2013.01); *C10M 2213/043* (2013.01); *C10N 2230/06* (2013.01); *C10N 2240/204* (2013.01)

(58) Field of Classification Search
USPC .......................................................... 508/106
See application file for complete search history.

(56) References Cited

U.S. PATENT DOCUMENTS

| | | |
|---|---|---|
| 2007/0224452 A1 | 9/2007 | Sasa et al. |
| 2010/0239887 A1 | 9/2010 | Kobayashi |
| 2012/0148875 A1 | 6/2012 | Hamakubo et al. |
| 2013/0209837 A1* | 8/2013 | Sagata ................ G11B 5/725 428/833 |
| 2014/0147699 A1 | 5/2014 | Kobayashi |
| 2016/0137947 A1 | 5/2016 | Isobe et al. |

FOREIGN PATENT DOCUMENTS

| | | |
|---|---|---|
| JP | 2009/301709 A | 12/2009 |
| JP | 2009-301709 A | 12/2009 |
| JP | 2010-086598 A | 4/2010 |
| JP | 2014-509677 A | 4/2014 |
| WO | 2009/066784 A1 | 5/2009 |
| WO | 2012/170009 A2 | 12/2012 |
| WO | 2012/170009 A3 | 12/2012 |
| WO | 2015/022871 A1 | 2/2015 |
| WO | 2015/022871 A9 | 2/2015 |

OTHER PUBLICATIONS

Extended European Search Report issued in corresponding European Patent Application No. 15862899.0 dated Apr. 10, 2018.
International Search Report issued in corresponding International Application No. PCT/JP2015/082882 dated Feb. 23, 2016.

* cited by examiner

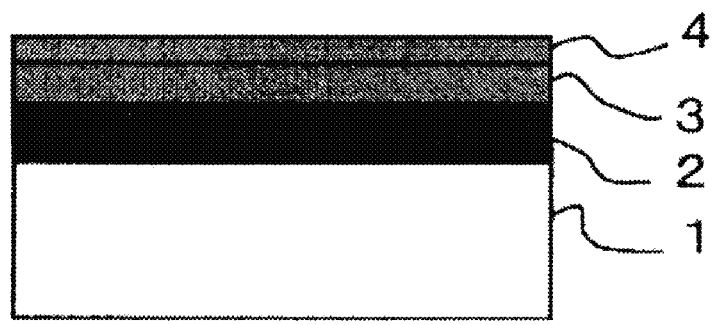

FLUOROPOLYETHER COMPOUND, LUBRICANT, MAGNETIC DISK, AND METHOD FOR PRODUCING SAME

This application is a 371 of PCT/JP2015/082882, filed Nov. 24, 2015.

TECHNICAL FIELD

The present invention relates to a fluoropolyether compound, a lubricant, a magnetic disk, and a method for producing the disk.

BACKGROUND ART

With the increasing recording density of magnetic disks, the distance between a magnetic disk serving as a recording medium and a head for recording and reproducing information has become almost nil as they approach coming into contact with each other. The magnetic disk surface is provided with a carbon protective film and a lubricant film (lubricant layer) to diminish abrasion caused by contact with the head or sliding of the head thereon, and to prevent contamination of the disk surface. Specifically, these two layers protect the surface of the magnetic disk. In particular, the lubricant layer provided on the top must have various properties, such as long-term stability, chemical resistance, friction properties, and heat resistance, and fluoropolyethers have been often used as a lubricant for magnetic disks (e.g., Patent Literature 1 and 2).

Recent years have seen the development of a technique called "heat-assisted magnetic recording" (HAMR), which aims to increase the recording density of magnetic disks. In HAMR, a recording spot is heated by laser irradiation immediately before writing. The heating temperature reaches 300° C. or more, and the lubricant on the magnetic disk is exposed to high heat. This evaporate, and the lubricity may not be maintained.

To prevent the evaporation of the lubricant at high temperatures, it is important to enhance the adsorption of the lubricant to the surface of magnetic disks. Patent Literature 3 and 4, for example, have proposed techniques to increase sites for adsorption to the magnetic disk by introducing hydroxyl groups into the molecule. However, these techniques are also still unsatisfactory in the bonds between the lubricant and the magnetic disk, and lubricants capable of forming stronger bonds with magnetic disks have been desired.

CITATION LIST

Patent Literature

Patent Literature 1: JP2009-301709A
Patent Literature 2: WO2009/066784
Patent Literature 3: JP2006-070173A
Patent Literature 4: JP2010-086598A

SUMMARY OF INVENTION

Technical Problem

An object of the present invention is to provide a fluoropolyether compound, a lubricant, and a magnetic disk that have such an excellent heat resistance as to be able to maintain the lubricity of the magnetic disk surface, without evaporating at high temperatures under laser heating, and also to provide a method for producing the disk.

Solution to Problem

The present inventors conducted extensive research, and found that the use of a fluoropolyether compound comprising an aliphatic hydrocarbon chain having a specific number of carbons and at least two perfluoropolyethers, each perfluoropolyether being ether-linked to the aliphatic hydrocarbon chain can achieve the object. The present invention has been completed on the basis of the findings.

The present invention relates to fluoropolyether compounds and the like described in the following Items 1 to 7.

Item 1.
A fluoropolyether compound comprising a $C_{4\text{-}10}$ aliphatic hydrocarbon chain present in the middle of the molecule and at least two perfluoropolyethers, each perfluoropolyether being ether-linked to the $C_{4\text{-}10}$ aliphatic hydrocarbon chain,
 the aliphatic hydrocarbon chain having at least one hydroxyl group,
 the at least two perfluoropolyethers having, at respective non-hydrocarbon chain terminals, at least one polar group selected from the group consisting of —OH, —OCH$_2$CH(OH)CH$_2$OH, —OCH$_2$CH(OH)CH$_2$OCH$_2$CH(OH)CH$_2$OH, —O(CH$_2$)$_m$OH, and —OCH$_2$(OH)CHCH$_2$—OC$_6$H$_4$—R$^1$ wherein m is an integer of 2 to 8, and R$^1$ represents hydrogen, $C_{1\text{-}4}$ alkoxy, amino, or an amide residue.

Item 2.
The fluoropolyether compound according to Item 1 wherein the aliphatic hydrocarbon chain has 8 carbon atoms.

Item 3.
The fluoropolyether compound according to Item 1 or 2 which is at least one member selected from the group consisting of
 HOCH$_2$CH(OH)CH$_2$OCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OCH$_2$CH(OH)CH$_2$OH,
 HOCH$_2$CH(OH)CH$_2$OCH$_2$CF$_2$CF$_2$O(CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$O)$_w$CF$_2$CF$_2$CF$_2$CH$_2$OCH$_2$CH(OH)CH$_2$OH,
 HOCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OH, and
 HOCH$_2$CF$_2$CF$_2$CF$_2$O(CF$_2$CF$_2$CF$_2$CF$_2$O)$_w$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OH.

Item 4.
The fluoropolyether compound according to Item 3 wherein z is a real number of 0 to 30, and w is a real number of 0 to 20.

Item 5.
A lubricant comprising the fluoropolyether compound according to any one of Items 1 to 4.

Item 6.
A magnetic disk comprising, in sequence over a substrate: a recording layer, a protective layer, and a lubricant layer, wherein the lubricant layer is formed by applying the lubricant according to Item 5 to the surface of the protective layer, and performing ultraviolet irradiation or heat treatment.

Item 7.

A method for producing a magnetic disk that comprises in sequence over a substrate, a recording layer, a protective layer, and a lubricant layer, the method comprising forming the recording layer and the protective layer over the substrate in this order, applying the lubricant according to Item 5 to the surface of the protective layer, and performing ultraviolet irradiation or heat treatment to form the lubricant layer.

Advantageous Effects of Invention

In the fluoropolyether compound according, to the present invention, at least one hydroxyl group contained in a $C_{4-10}$ aliphatic hydrocarbon chain present in the middle of the molecule and at least one polar group present at respective non-hydrocarbon chain terminals of the perfluoropolyethers can bond to the surface of magnetic disks. In addition, the bonds between the carbon atoms of the $C_{4-10}$ aliphatic hydrocarbon chain and the oxygen atoms are cleaved by ultraviolet irradiation or heat treatment, and firm bonds are formed with the surface of a magnetic disk. This reduces or prevents the evaporation of the compound by heating, and maintains the lubricity of the magnetic disk surface.

Thus, a lubricant comprising the fluoropolyether compound according to the present invention can maintain the lubricity of the surface of magnetic disks at high temperatures under laser heating.

BRIEF DESCRIPTION OF DRAWINGS

FIG. 1 is a cross-sectional diagram illustrating a magnetic disk according to the present invention.

DESCRIPTION OF EMBODIMENTS

In the fluoropolyether compound according to the present invention, a $C_{4-10}$ aliphatic hydrocarbon chain present in the middle of the molecule is ether-linked to at least two perfluoropolyethers, and the aliphatic hydrocarbon chain has at least one hydroxyl group. The at least two perfluoropolyethers each have, at their non-hydrocarbon chain terminals, at least one polar group selected from the group consisting of —OH, —OCH$_2$CH(OH)CH$_2$OH, —OCH$_2$CH(CH)CH$_2$OCH$_2$CH(OH)CH$_2$OH, —O(CH$_2$)$_m$OH, and —OCH$_2$(OH)CHCH$_2$—OC$_6$H$_4$—R$^1$ wherein m is an integer of 2 to 8; and R$^1$ represents hydrogen, C$_{1-4}$ alkoxy, amino, or an amide residue.

The aliphatic hydrocarbon chain present in the middle of the molecule has 4 to 10 carbon atoms, preferably 4 to 8 carbon atoms, and particularly preferably 8 carbon atoms. In the present invention, it is an important feature that the aliphatic hydrocarbon chain has 4 to 10 carbon atoms. In the case of an aliphatic hydrocarbon chain having 4 or more carbon atoms, ultraviolet irradiation or heat treatment cleaves the compound between the carbon atoms of the $C_{4-10}$ aliphatic hydrocarbon chain and the oxygen atoms, and CH$_2$ at each terminal of the hydrocarbon and/or oxygen atoms (O) remaining in the perfluoropolyethers after cleavage can firmly bond to a magnetic disk.

The aliphatic hydrocarbon chain encompasses both linear and branched chains. In the case of a linear hydrocarbon, both terminals of the chain are linked to respective perfluoropolyethers through respective oxygen atoms. In the case of a branched-chain hydrocarbon, both terminals of the main chain and the terminal of at least one branched chain can be ether-linked to respective perfluoropolyethers. When the number of the branched-chain is, for example, 1, the hydrocarbon can be ether-linked to 3 perfluoropolyethers. When the number of the branched-chain is 2, the hydrocarbon can be ether-linked to 4 perfluoropolyethers.

Perfluoropolyether skeletons typically used in lubricants for magnetic disks can be used for the perfluoropolyethers, without any limitation. The perfluoropolyethers, are a portion represented by, for example, —CH$_2$(CF$_2$)$_p$O(CF$_2$O)$_x$(CF$_2$CF$_2$O)$_y$(CF$_2$CF$_2$CF$_2$O)$_z$(CF$_2$CF$_2$CF$_2$CF$_2$O)$_w$(CF$_2$)$_p$CH$_2$— wherein x and y are each a real number of 0 to 30; z is a real number of 0 to 30; w is a real number of 0 to 20; and p is an integer of 1 to 3. Here, x and y are each preferably a real number of 0 to 12, and more preferably a real number of 2 to 8. When x and y are both a real number of 2 to 8, the molecular chain becomes flat, providing a lubricant that can form a thin film; thus, it is preferable that x and y are both a real number of 2 to 8. Here, z is preferably a real number of 1 to 12, and more preferably a real number of 2 to 8. When z is a real number of 2 to 8, the molecular chain becomes flat, providing a lubricant that can form a thin film; thus it is preferable that z is a real number of 2 to 8. Here, w is preferably a real number of 0 to 10, and more preferably a real number of 1 to 5. When w is a real number of 1 to 5, the molecular chain becomes flat, providing a lubricant that can form a thin film; thus it is preferable that w is a real number of 1 to 5. Here, p is an integer of 1 to 3.

Each of the non-hydrocarbon chain terminals of the perfluoropolyethers has at least one polar group selected from the group consisting of —OH, —OCH$_2$CH(OH)OCH$_2$OH, —OCH$_2$CH(OH)CH$_2$OCH$_2$CH(OH)CH$_2$OH, —O(CH$_2$)$_m$OH, and —OCH$_2$(OH)CHCH$_2$—OC$_6$H$_4$—R$^1$ wherein m is an integer of 2 to 8; and R$^1$ represents hydrogen, C$_{1-4}$ alkoxy, amino, or an amide residue. The at least one polar group is a functional group that interacts with the surface of magnetic disks. The at least one polar group is weakly bonded to the surface of magnetic disks before ultraviolet irradiation or heat treatment, but can be firmly bonded to the surface when exposed to ultraviolet irradiation or heat treatment.

The compound according to the present invention can be obtained, for example, by reacting an aliphatic hydrocarbon having two epoxy groups (A) with a linear fluoropolyether having a hydroxyl group at one terminal and a hydroxy-containing alkoxy group at the other terminal (a), or a linear fluoropolyether having a hydroxyl group at each terminal (d). Specifically, the compound can be synthesized by the following method.

[1] First, fluoropolyether (a) is synthesized (first step).

A linear fluoropolyether having a hydroxyl group at each terminal (b) is reacted with a compound that reacts with hydroxyl groups to form a hydroxy-containing alkoxy (c). The reaction temperature is 20 to 90° C., and preferably 60 to 80° C. The reaction time is 5 to 20 hours, and preferably 10 to 15 hours. The amount of compound (c) for use is preferably 0.5 to 1.5 equivalents relative to fluoropolyether (b). The reaction product is then, for example, purified by column chromatography to obtain fluoropolyether (a). The reaction may be performed in a solvent. The solvent for use includes t-butyl alcohol, dimethyl formaldehyde, 1,4-dioxane, dimethyl sulfoxide, and dimethylacetamide. The reaction may be performed using a reaction accelerator. Examples of reaction accelerators include basic compounds, such as sodium, potassium t-butoxide, and sodium hydride.

Fluoropolyether (b) is HOCH$_2$—(CF$_2$)$_p$O(CF$_2$O)$_x$(CF$_2$CF$_2$O)$_y$(CF$_2$CF$_2$CF$_2$)$_z$(CF$_2$CF$_2$CF$_2$CF$_2$O)$_w$(CF$_2$)$_p$—CH$_2$OH wherein x and y are each a real number of 0 to 30;

z is a real number of 0 to 30; w is a real number of 0 to 20; and p is an integer of 1 to 3. Specific examples of fluoropolyether (b) include compounds represented by $HOCH_2CF_2CF_2CF_2O(CF_2CF_2CF_2CF_2O)_wCF_2CF_2CF_2CH_2OH$, compounds represented by $HOCH_2CF_2O(CF_2O)_x(CF_2CF_2O)_yCF_2CH_2OH$, and compounds represented by $HOCH_2CF_2CF_2O(CF_2CF_2CF_2O)_zCF_2CF_2CH_2OH$. These fluoropolyethers have a number average molecular weight of typically 300 to 4000, preferably 500 to 2000, and more preferably 600 to 1500. The number average molecular weight here is a value obtained by measurement of $^{19}F$-NMR with JNM-ECX400 (JEOL Ltd). In NMR measurement, the samples were used as they were, without dilution with a solvent. Known peaks, part of the skeleton of the fluoropolyethers, were used as the standard for chemical shift. Here, x and y are each a real number of 0 to 30, and preferably a real number of 0 to 12. When x and y are both a real number of 0 to 12, the molecular chain becomes flat, thereby providing a lubricant that can form a thin film; thus it is preferable that x and y are both a real number of 0 to 12. Here, Z is a real number of 0 to 30, and preferably a real number of 1 to 12. When z is a real number of 1 to 12, the molecular chain becomes flat, thereby providing a lubricant that can form a thin film; thus it is preferable that z is a real number of 1 to 12. Here, w is a real number of 0 to 20, and preferably a real number of 0 to 10. When w is a real number of 0 to 10, the molecular chain becomes flat, thereby providing a lubricant that can form a thin film; thus it is preferable that w is a real number of 0 to 10. Here, p is an integer of 1 to 3.

Fluoropolyether (b) has a molecular weight distribution. The molecular weight distribution (PD) represented by weight average molecular weight/number average molecular weight of fluoropolyether (b) is 1.0 to 1.5, preferably 1.0 to 1.3, and more preferably 1.0 to 1.1. The molecular weight distribution is a characteristic value obtained using HPLC-8220GPC (Tosoh Corporation), a column (PLgel Mixed E, Polymer Laboratories Ltd.), an HCFC-based chlorofluorocarbon alternative as an eluent, and a perfluoropolyether with no functional groups as the standard substance.

Examples of compound (c) include epoxy-containing compounds, haloalkyl alcohols represented by $X(CH_2)_mOH$, and epoxy-containing phenoxy compounds (c-1).

Examples of epoxy-containing compounds include glycidol, propylene oxide, glycidyl methyl ether, and isobutylene oxide.

In haloalkyl alcohols represented by $X(CH_2)_mOH$, X represents a halogen atom, such as chlorine, bromine, and iodine, and m is a real number of 2 to 8. Examples of haloalkyl alcohols include 2-chloroethanol, 3-chloropropanol, 4-chlorobutanol, 5-chloropentanol, 6-chlorohexanol, 7-chloroheptanol, 8-chlorooctanol, 2-bromoethanol, 3-bromopropanol, 4-bromobutanol, 5-bromopentanol, 6-bromohexanol, 7-bromoheptanol, 8-bromooctanol, 2-iodoethanol, 3-iodopropanol, 4-iodobutanol, 5-iodopentanol, 6-iodohexanol, 7-iodoheptanol, and 8-iodooctanol.

Epoxy-containing phenoxy compound (c-1) is represented, for example, by the following formula:

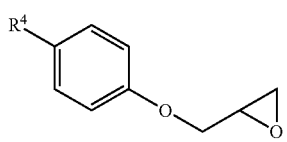

(c-1)

Examples of $R^4$ includes hydrogen, alkoxy, amino, and an amide residue.

Examples of $C_{1-4}$ alkoxy include methoxy, ethoxy, propoxy, and butoxy. Examples of amino groups include amino, methylamino, dimethylamino, ethylamino, and diethylamino. Examples of amide residues include acetamide ($-NHCOCH_3$) and propionamide ($-NHCOC_2H_5$).

Specific examples of compound (c-1) include glycidyl 4-methoxyphenyl ether, glycidyl 4-ethoxyphenyl ether, glycidyl 4-propoxyphenyl ether, glycidyl 4-butoxyphenyl ether, glycidyl 4-aminophenyl ether, glycidyl 4-methylaminophenyl ether, glycidyl 4-dimethylaminophenyl ether, glycidyl 4-ethylaminophenyl ether, glycidyl 4-diethylaminophenyl ether, glycidyl 4-acetamidophenyl ether, and glycidyl 4-propionamidephenyl ether.

For example, the use of $HOCH_2CF_2O(CF_2O)_x(CF_2CF_2O)_yCF_2CH_2OH$ as fluoropolyether (b) and glycidol as compound (c) generates, through their reaction, $HOCH_2CH(OH)CH_2OCH_2CF_2O(CF_2O)_x(CF_2CF_2O)_yCF_2CH_2OH$, $HOCH_2CH(OH)CH_2OCH_2CH(OH)CH_2OCH_2CF_2O(CF_2CF_2O)_y(CF_2O)_xCF_2CH_2OH$, and the like, as fluoropolyether (a).

The use of $HOCH_2CF_2O(CF_2O)_x(CF_2CF_2O)_yCF_2CH_2OH$ as fluoropolyether (b) and 2-bromoethanol as compound (c) generates $HOCH_2CH_2OCH_2CF_2O(CF_2O)_x(CF_2CF_2O)_yCF_2CH_2OH$ as fluoropolyether (a).

The use of $HOCH_2CF_2O(CF_2O)_x(CF_2CF_2O)_yCF_2CH_2OH$ as fluoropolyether (b) and glycidyl 4-methoxyphenyl ether as compound (c) generates $CH_3O-C_6H_4O-CH_2CH(OH)CH_2OCH_2CF_2O(CF_2O)_x(CF_2CF_2O)_yCF_2CH_2OH$ as fluoropolyether (a).

When fluoropolyether (b) is reacted with aliphatic hydrocarbon (A), the first step can be skipped, and the following second step is performed.

[2] Subsequently, the compound of the present invention is synthesized by reacting aliphatic hydrocarbon (A) with fluoropolyether (a) obtained in the first step or fluoropolyether (b) (second step).

Aliphatic hydrocarbon (A) is reacted with fluoropolyether (a) obtained in the first step or fluoropolyether (b) in the presence of a base. The reaction temperature is 20 to 90° C., and preferably 60 to 80° C. The reaction time is 5 to 20 hours, and preferably 10 to 15 hours. It is preferable to use 0.5 to 1.5 equivalents of aliphatic hydrocarbon (A) and 0.5 to 2.0 equivalents of a base, relative to fluoropolyether (a) or (b). Bases for use include sodium t-butoxide, potassium t-butoxide, sodium hydroxide, potassium hydroxide, and sodium hydride. The reaction can be performed in a solvent. Solvents for use include t-Butanol, toluene, and xylene. Thereafter, washing with water and dehydration, for example, are performed. The compound of the present invention is finally provided.

Specific examples of aliphatic hydrocarbon include 1,3-butadiene diepoxide, 1,4-pentadiene diepoxide, 1,5-hexadiene diepoxide, 1,6-heptadiene diepoxide, 1,7-octadiene diepoxide, 1,8-nonadiene diepoxide, 1,9-decane diepoxide, 1,10-undecane diepoxide, 1,11-dodecane diepoxide, and 1,1,1,1-tetra(glycidyl oxymethyl)methane.

Reaction of fluoropolyether (a) obtained in the first step with aliphatic hydrocarbon (A) specifically provides compounds, such as $HOCH_2CH(OH)CH_2OCH_2CF_2CF_2O(CF_2CF_2CF_2O)_zCF_2CF_2CH_2-OCH_2CH(OH)CH_2CH_2CH_2CH_2CH(OH)CH_2O-CH_2CF_2CF_2O(CF_2CF_2CF_2O)_zCF_2CF_2CH_2OCH_2CH(OH)CH_2OH$ and $HOCH_2CH(OH)CH_2OCH_2CF_2CF_2CF_2O(CF_2CF_2CF_2CF_2O)_wCF_2CF_2CF_2CH_2-OCH_2CH(OH)$ $CH_2CH_2CH_2CH_2CH(OH)CH_2O\!\!-\!\!CH_2CF_2CF_2CF_2O$ $(CF_2CF_2CF_2CF_2O)_wCF_2CF_2CF_2CH_2OCH_2CH(OH)$ $CH_2OH$.

Reaction of fluoropolyether (b) with aliphatic hydrocarbon (A) specifically provides compounds, such as $HOCH_2CF_2CF_2O(CF_2CF_2CF_2O)_zCF_2CF_2CH_2\!\!-\!\!OCH_2CH$ $(OH)CH_2CH_2CH_2CH_2CH(OH)CH_2O\!\!-\!\!CH_2CF_2CF_2O$ $(CF_2CF_2CF_2O)_zCF_2CF_2CH_2OH$ and $HOCH_2CF_2CF_2CF_2O$ $(CF_2CF_2CF_2CF_2O)_wCF_2CF_2CF_2CH_2\!\!-\!\!OCH_2CH(OH)$ $CH_2CH_2CH_2CH_2CH(OH)CH_2O\!\!-\!\!CH_2CF_2CF_2CF_2O$ $(CF_2CF_2CF_2CF_2O)_wCF_2CF_2CF_2CH_2OH$.

The fluoropolyether compound of the present invention can bind to the surface of a magnetic disk through at least one hydroxyl group of the $C_{4\text{-}10}$ aliphatic hydrocarbon chain present in the middle of the molecule and at least one polar group present at respective non-hydrocarbon chain terminals of the perfluoropolyethers. In addition, the bonds between the carbon atoms of the $C_{4\text{-}10}$ aliphatic hydrocarbon chain and the oxygen atoms are cleaved by ultraviolet irradiation or heat treatment, and strong bonds are formed with the surface of the magnetic disk, thus reducing the evaporation of the compound by heat, and maintaining the lubricity of the magnetic disk surface. A lubricant comprising the fluoropolyether compound of the present invention therefore can maintain the lubricity of the magnetic disk surface at high temperatures under laser heating.

Before applying the compound of the present invention to the surface of a magnetic disk, it is preferable to dilute the compound with a solvent. Examples of the solvent include PF-5060, PF-5080, HFE-7100, HFE-7200 (3M); and Vertrel-XF (DuPont). The diluted lubricant has a concentration of 1 wt % or less, and preferably 0.001 to 0.1 wt %.

The compound of the present invention can be used singly, and can also be used in combination at any ratio with a fluoropolyether-based lubricant typically used in lubricants for magnetic disks, such as Fomblin Ztetraol, Zdol TX, AM, (Solvay Solexis), Demnum (Daikin Industries, Ltd.), and Krytox (Dupont).

The compound of the present invention can be used as a lubricant to reduce the spacing between a magnetic disk and a head inside a magnetic disk apparatus and improve the durability against sliding. The lubricant of the present invention has excellent heat resistance, and is thus suitable for magnetic disks in hard disk drives (HDD) using an HAMR technique. Thus, the compound is usable for not only magnetic disks, but also magnetic heads, photomagnetic recording devices, and magnetic tapes, all three of which have a carbon protective film, surface protective films for organic materials, such as plastics, and surface protective films for inorganic materials, such as $Si_3N_4$, SiC, and $SiO_2$.

FIG. 1 is a cross-sectional diagram showing a magnetic disk according to the present invention. The magnetic disk of the present invention comprises a recording layer 2 formed on a substrate 1, a protective layer 3 formed on the recording layer 2, and a lubricant layer 4, which comprises the compound of the present invention and a lubricant for magnetic disks, formed on the protective layer 3 as the outermost layer. Examples of the substrate 1 include aluminium alloys, ceramics such as glass, and polycarbonate. The recording layer 2 may comprise 2 or more layers.

Examples of constituent materials for a magnetic layer, which is the recording layer of the magnetic disk, include primarily elements capable of forming a ferromagnet, such as iron, cobalt, and nickel; alloys containing chromium, platinum, tantalum, or the like in addition to such elements; and oxides thereof. The layer of these materials is formed by a technique such as plating and sputtering. Examples of materials for the protective layer include SiC and $SiO_2$. The layer of these materials is formed by sputtering or CVD.

Lubricant layers presently available have a thickness of 30 Å or less. When a lubricant having a viscosity of about 100 mPa·s or more at 20° C. is applied as it is, the resulting film could have an excessively large thickness. Thus, such a lubricant is dissolved in a solvent for use in coating. In either case where the compound of the present invention is used as a lubricant singly or mixed with other lubricants, the lubricant of the present invention dissolved in a solvent makes it easier to desirably control the film thickness. However, the concentration varies depending on the coating technique and conditions, the mixing ratio, and the like. The thickness of a film formed by the lubricant of the present invention is preferably 5 to 15 Å.

To form a strong bond between the lubricant and the magnetic disk, it is preferable to, after applying the lubricant to the surface of the magnetic disk, subject the surface of the magnetic disk to ultraviolet irradiation or heat treatment. When performing ultraviolet irradiation, it is preferable to use ultraviolet rays having a wavelength of 185 nm or 254 nm as the dominant wavelength. The temperature of the heat treatment is preferably about 120 to 170° C. Performing ultraviolet irradiation or heat treatment can further reduce the evaporation of the lubricant by heat.

A preferable magnetic disk of the present invention comprises in sequence over a substrate, a recording layer, a protective layer, and a lubricant layer, wherein the lubricant layer is formed by applying the fluoropolyether-containing lubricant to the surface of the protective layer, and performing ultraviolet irradiation or heat treatment.

The method for producing this magnetic disk includes a method for producing a magnetic disk that comprises in sequence over a substrate, a recording layer, a protective layer, and a lubricant layer, and the method comprises forming a recording layer and a protective layer over a substrate in this order, applying the fluoropolyether-containing lubricant to the surface of the protective layer, and performing ultraviolet irradiation or heat treatment to form a lubricant layer.

The magnetic disk of the present invention can be used in a magnetic disk apparatus that comprises: a magnetic disk drive that stores the disk, and that is equipped with a magnetic head for recording, reproducing, and erasing information, a motor for rotating the disk etc.; and a control system for controlling the drive.

The magnetic disk according to the present invention and a magnetic disk apparatus comprising the magnetic disk can be used, for example, as an external memory for computers, word processors etc. The disk and apparatus can also be used in various devices, such as navigation systems, game consoles, cellular phones, and PHS; internal or external recording devices for building security, power plant administration systems, power plant control systems; and the like.

EXAMPLES

The following Examples will describe the present invention in detail. However, the present invention is not limited to the Examples. Note that $^{19}$F-NMR was measured without a solvent, and using as the standard chemical shift a known peak that is a portion of the backbone structure of a fluoropolyether, and that $^1$H-NMR was measured without a solvent and using $D_2O$ as the standard substance.

Example 1

Synthesis of $HOCH_2CH(OH)CH_2OCH_2CF_2CF_2O$ $(CF_2CF_2CF_2O)_zCF_2CF_2CH_2\!\!-\!\!OCH_2CH(OH)CH_2CH_2CH_2$ $CH_2CH(OH)CH_2O$—$CH_2CF_2CF_2O(CF_2CF_2CF_2O)_zCF_2$ $CF_2CH_2OCH_2CH(OH)CH_2OH$ (Compound 1)

In an argon atmosphere, a mixture of t-butyl alcohol (41 g), 95 g of a fluoropolyether represented by HO—$CH_2CF_2CF_2O(CF_2CF_2CF_2O)_zCF_2CF_2CH_2$—OH (the number average molecular weight: 1980, the molecular weight distribution: 1.25), potassium t-butoxide (0.6 g), and glycidol (3.6 g) was stirred at 70° C. for 14 hours. Subsequently, the mixture was washed with water, dehydrated, and purified by silica gel column chromatography, thereby giving 95 g of a perfluoropolyether having one hydroxyl group at one terminal and two hydroxyl groups at the other terminal (the average molecular weight: 2110). This compound (95 g) was dissolved in meta-xylene hexafluoride (95 g), and sodium hydroxide (3.0 g) and 1,7-octadienediepoxide (3.2 g) were added thereto, followed by stirring at 70° C. for 14 hours. The mixture was then washed with water, dehydrated, and purified by distillation, thereby giving 60 g of compound 1.

Compound 1 was a colorless transparent liquid, and had a density of 1.74 q/cm³ at 20° C. Compound 1 was identified by NMR as shown below.

$^{19}$F-NMR (solvent: none, standard substance: $OCF_2CF_2CF_2O$ in the obtained product, which was taken as −129.7 ppm)

δ=−129.7 ppm
[18F, —$OCF_2CF_2CF_2O$—],
δ=−83.7
[36F, —$OCF_2CF_2CF_2O$—],
δ=−124.2 ppm
[8F, —$OCF_2CF_2CH_2OCH_2CH(OH)CH_2CH_2CH_2CH(OH)CH_2$—, —$OCF_2CF_2CH_2OCH_2CH(OH)CH_2OH$],
δ=−86.5 ppm
[8F, —$OCF_2CF_2CH_2OCH_2CH(OH)CH_2CH_2CH_2CH(OH)CH_2$—, —$OCF_2CF_2CH_2OCH_2CH(OH)CH_2O$],
z=9.3

$^1$H-NMR (solvent: none, standard substance: $D_2O$)
δ=3.2 to 3.8 ppm
[30H, HOCH_2CH(OH)CH_2OCH_2CF_2CF_2O(CF_2CF_2CF_2O)_zCF_2CF_2CH_2—OCH_2CH(OH)CH_2CH_2CH_2CH_2CH(OH)CH_2O—CH_2CF_2CF_2O(CF_2CF_2CF_2O)_zCF_2CF_2CH_2OCH_2CH(OH)CH_2OH]
δ=1.1 ppm.
[8H, HOCH_2CH(OH)CH_2OCH_2CF_2CF_2(CF_2CF_2CF_2O)_zCF_2CF_2CH_2—OCH_2CH(OH)CH_2CH_2CH_2CH_2CH(OH)CH_2O—CH_2CF_2CF_2O(CF_2CF_2CF_2O)_zCF_2CF_2CH_2OCH_2CH(OH)CH_2OH]

Example 2

Synthesis of $HOCH_2CH(OH)CH_2OCH_2CF_2CF_2CF_2O(CF_2CF_2CF_2CF_2O)_wCF_2CF_2CF_2CH_2$—$OCH_2CH(OH)CH_2CH_2CH_2CH_2CH(OH)O$—$CH_2CF_2CF_2CF_2O(CF_2CF_2CF_2CF_2O)_wCF_2CF_2CF_2CH_2OCH_2CH(OH)CH_2OH$ (Compound 2)

The procedure of Example 1 was repeated except that a fluoropolyether represented by HO—$CH_2CF_2CF_2O(CF_2CF_2CF_2CF_2O)_wCF_2CF_2CF_2$—$CH_2$—OH was used instead of the fluoropolyether represented by HO—$CH_2CF_2CF_2O(CF_2CF_2CF_2O)_zCF_2CF_2CH_2$—OH used in Example 1, thereby giving 58 g of compound 2.

Compound 2 was a colorless transparent liquid, and had a density of 1.77 g; cm³ at 20° C. Compound 2 was identified by NMR as shown below.

$^{19}$F-NMR (solvent: none, standard substance: $OCF_2CF_2CF_2O$ in the obtained product, which was taken as −125.8 ppm)

δ=−83.7 ppm
[32F, —$OCF_2CF_2CF_2CF_2O$—, —$OCF_2CF_2CF_2CH_2OCH_2CH(OH)CH_2CH_2CH_2CH_2CH(OH)CH_2$—, —$OCF_2CF_2CF_2CH_2OCH_2CH(OH)CH_2OH$],
δ=−120.5 ppm
[12F, —$OCF_2CF_2CF_2CH_2OCH_2CH(OH)CH_2CH_2CH_2CH_2CH(OH)CH_2$—, —$OCF_2CF_2CF_2CH_2OCH_2CH(OH)CH_2OH$],
δ=−125.8 ppm
[24F, —$OCF_2CF_2CF_2CF_2O$—],
δ=−127.6 ppm
[8F, —$OCF_2CF_2CF_2CH_2OCH_2CH(OH)CH_2CH_2CH_2CH(OH)CH_2$—, —$OCF_2CF_2CF_2CH_2OCH_2CH(OH)CH_2OH$]
w=3.0

$^1$H-NMR (solvent: none, standard substance: $D_2O$)
δ=3.2 to 3.8 ppm
[30H, HOCH_2CH(OH)CH_2OCH_2CF_2CF_2CF_2O(CF_2CF_2CF_2CF_2O)_wCF_2CF_2CF_2CH_2—OCH_2CH(OH)CH_2CH_2CH_2CH_2CH(OH)CH_2O—CH_2CF_2CF_2CF_2O(CF_2CF_2CF_2CF_2O)_wCF_2CF_2CF_2CH_2OCH_2CH(OH)CH_2OH]
δ=1.1 ppm
[8H, HOCH_2CH(OH)CH_2OCH_2CF_2CF_2CF_2O(CF_2CF_2CF_2CF_2O)_wCF_2CF_2CF_2CH_2—OCH_2CH(OH)CH_2CH_2CH_2CH(OH)CH_2O—CH_2CF_2CF_2CF_2O(CF_2CF_2CF_2CF_2O)_wCF_2CF_2CF_2CH_2OCH_2CH(OH)CH_2OH]

Example 3

Synthesis of $HOCH_2CF_2CF_2O(CF_2CF_2CF_2O)_zCF_2CF_2CH_2$—$OCH_2CH(OH)CH_2CH_2CH_2CH_2CH(OH)CH_2O$—$CH_2CF_2CF_2O(CF_2CF_2CF_2O)_zCF_2CF_2CH_2OH$ (Compound 3)

In an argon atmosphere, 80 g of a fluoropolyether represented by HO—$CH_2CF_2CF_2O(CF_2CF_2CF_2O)_zCF_2CF_2CH_2$—OH (the number average molecular weight: 1890, the molecular weight distribution: 1.20) was dissolved in meta-xylene hexafluoride (80 g), and sodium hydroxide (2.4 g) and 1,7-octadienediepoxide (2.6 g) were added thereto, followed by stirring at 70° C. for 14 hours. The mixture was then washed with water, dehydrated, and purified by distillation, thereby giving 55 g of compound 3.

Compound 3 was a colorless transparent liquid, and had a density of 1.70 g/cm³ at 20° C. Compound 3 was identified by NMR as shown below.

$^{19}$F-NMR (solvent: none, standard substance: $OCF_2CF_2CF_2O$ in the obtained product, which was taken as −129.7 ppm)

δ=−129.7 ppm
[36F, —$OCF_2CF_2CF_2O$—],
δ=−83.7
[72F, —$OCF_2CF_2CF_2O$—],
δ=−124.2 ppm
[4F, —$OCF_2CF_2CH_2OCH_2CH(OH)CH_2CH_2CH_2CH(OH)CH_2$—],
δ=−126.4 ppm
[4F, —$OCF_2CF_2CH_2OH$],
δ=−86.5 ppm
[8F, —$OCF_2CF_2CH_2OCH_2CH(OH)CH_2CH_2CH_2CH(OH)CH_2$—, —$OCF_2CF_2CH_2OCH_2CH(OH)CH_2OH$]
z=9.1

$^1$H-NMR (solvent: none, standard substance: $D_2O$)

δ=3.2 to 3.8 ppm

[18H, HOC$\underline{H}_2$CF$_2$CF$_2$O(CF$_2$CF$_2$CF$_2$O)$_z$CF$_2$CF$_2$C$\underline{H}_2$—OC$\underline{H}_2$C$\underline{H}$(O$\underline{H}$)CH$_2$CH$_2$CH$_2$C$\underline{H}$(O$\underline{H}$)C$\underline{H}_2$O—C$\underline{H}_2$O(CF$_2$CF$_2$CF$_2$O)$_z$CF$_2$CF$_2$C$\underline{H}_2$OH]

δ=1.1 ppm

[8H, HOCH$_2$CF$_2$O(CF$_2$CF$_2$CF$_2$O)$_z$CF$_2$CF$_2$CH$_2$—OCH$_2$CH(OH)C$\underline{H}_2$C$\underline{H}_2$C$\underline{H}_2$C$\underline{H}_2$CH(OH)CH$_2$O—CH$_2$CF$_2$CF$_2$O(CF$_2$CF$_2$CF$_2$O)$_z$CF$_2$CF$_2$CH$_2$OH]

Example 4

Synthesis of HOCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OH (Compound 4)

The procedure of Example 3 was repeated except that a fluoropolyether represented by HO—CH$_2$CF$_2$CF$_2$O(CF$_2$CF$_2$CF$_2$CF$_2$O)$_w$CF$_2$CF$_2$CF$_2$—CH$_2$—OH was used instead of the fluoropolyether represented by HO—CH$_2$CF$_2$CF$_2$O(CF$_2$CF$_2$CF$_2$O)$_z$CF$_2$CF$_2$CH$_2$—OH used in Example 3, thereby giving 45 g of compound 4.

Compound 4 was a colorless transparent liquid, and had a density of 1.72 g/cm$^3$ at 20° C. Compound 4 was identified by NMR as shown below.

$^{19}$H-NMR (solvent: none, standard substance: OCF$_2$CF$_2$CF$_2$O in the obtained product, which was taken as −125.8 ppm)

δ=−83.7 ppm

[32F, —OC$\underline{F}_2$CF$_2$CF$_2$C$\underline{F}_2$O, —OC$\underline{F}_2$CF$_2$CF$_2$CH$_2$OCH$_2$CH(OH)CH$_2$CH$_2$CH$_2$CH$_2$CH(OH)CH$_2$—, —OC$\underline{F}_2$CF$_2$CF$_2$CH$_2$OH], δ=−120.5 ppm

[4F, —OCF$_2$CF$_2$C$\underline{F}_2$CH$_2$OCH$_2$CH(OH)CH$_2$CH$_2$CH$_2$CH(OH)CH$_2$—], δ=−122.8 ppm

[4F, —OCF$_2$CF$_2$C$\underline{F}_2$CH$_2$OH],

δ=−125.8 ppm

[24F, —OCF$_2$C$\underline{F}_2$CF$_2$O—],

δ=−127.6 ppm

[8F, —OCF$_2$C$\underline{F}_2$CF$_2$OCH$_2$CH(OH)CH$_2$CH$_2$CH$_2$CH(OH)CH$_2$—, —OCF$_2$C$\underline{F}_2$CF$_2$CH$_2$CH(OH)CH$_2$OH]

w=3.0

$^1$H-NMR (solvent: none, standard substance: D$_2$O)

δ=3.2 to 3.8 ppm

[18H, HOC$\underline{H}_2$CF$_2$CF$_2$CF$_2$O(CF$_2$CF$_2$CF$_2$CF$_2$O)$_w$CF$_2$CF$_2$CF$_2$C$\underline{H}_2$—OC$\underline{H}_2$C$\underline{H}$(O$\underline{H}$)CH$_2$CH$_2$CH$_2$CH$_2$C$\underline{H}$(O$\underline{H}$)C$\underline{H}_2$O—C$\underline{H}_2$CF$_2$CF$_2$CF$_2$O(CF$_2$CF$_2$CF$_2$CF$_2$O)$_w$CF$_2$CF$_2$C$\underline{H}_2$O$\underline{H}$]

δ=1.1 ppm

[8H, HOCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH$_2$(OH)C$\underline{H}_2$C$\underline{H}_2$C$\underline{H}_2$C$\underline{H}_2$CH(OH)CH$_2$O—CH$_2$CF$_2$CF$_2$O(CF$_2$CF$_2$CF$_2$O)$_w$CF$_2$CF$_2$CF$_2$CH$_2$OH]

For comparison, the following compounds 5 to 7 were used.

Compound 5 is HOCH$_2$CH(OH)CH$_2$OCH$_2$CF$_2$O(CF$_2$O)$_x$(CF$_2$CF$_2$O)$_y$CF$_2$CH$_2$OCH$_2$CH(OH)CH$_2$OCH$_2$CF$_2$O(CF$_2$O)$_x$(CF$_2$CF$_2$O)$_y$CF$_2$CH$_2$OCH$_2$CH(OH)CH$_2$OH, which was produced in accordance with the following production method.

In an argon atmosphere, a mixture of t-butyl alcohol (39 g), 90 g of a fluoropolyether represented by HO—CH$_2$CF$_2$O(CF$_2$O)$_x$(CF$_2$CF$_2$)$_y$CF$_2$CH$_2$—OH (the number average molecular weight: 1350, the molecular weight distribution: 1.25), potassium t-butoxide (0.7 g), and glycidol (5 g) was stirred at 70° C. for 14 hours. The mixture was then washed with water, dehydrated, and purified by silica gel column chromatography, thereby giving a compound having one hydroxyl group at one terminal and two hydroxyl groups at the other terminal. This compound (85 g) was dissolved in t-butyl alcohol (57 g), and potassium t-butoxide (3.6 g) and epichlorohydrin (3.7 g) were added thereto, followed by stirring at 70° C. for 14 hours. The mixture was then washed with water, dehydrated, and purified by distillation, thereby giving 60 g of compound 5.

Compound 5 was a colorless transparent liquid, and had a density of 1.74 g/cm$^3$ at 20° C. Compound 5 was identified by NMR as shown below.

$^{19}$F-NMR (solvent: none, standard substance: OCF$_2$C$\underline{F}_2$CF$_2$CF$_2$O in the obtained product, which was taken as −125.8 ppm)

δ=−52.1 ppm, −53.7 ppm, −55.4 ppm

[24F, —OC$\underline{F}_2$O—],

δ=−89.1 ppm, −90.7 ppm

[48F, —OC$\underline{F}_2$C$\underline{F}_2$O—],

δ=−77.9 ppm, −80.0 ppm

[8F, —OC$\underline{F}_2$CH$_2$OCH$_2$CH(OH)CH$_2$O—, —OCF$_2$CH$_2$OCH$_2$CH(OH)CH$_2$OH], x=6.2, y=6.1

$^{19}$H-NMR (solvent: none, standard substance: D$_2$O)

δ=3.2 to 3.8 ppm

[28H, HOC$\underline{H}_2$C$\underline{H}$(O$\underline{H}$)C$\underline{H}_2$OC$\underline{H}_2$—CF$_2$O(CF$_2$O)$_x$(CF$_2$CF$_2$O)$_y$CF$_2$C$\underline{H}_2$—, —O—C$\underline{H}_2$C$\underline{H}$(O$\underline{H}$)C$\underline{H}_2$O—]

Compound 6 is a compound represented by HOCH$_2$CH(OH)CH$_2$OCH$_2$CF$_2$O(CF$_2$CF$_2$O)$_x$(CF$_2$O)$_y$CF$_2$CH$_2$OCH$_2$CH(OH)CH$_2$OH, and is also called Fomblin Ztetraol (produced by Solvey Solexis, trade name), which is a typical lubricant for magnetic disks. Compound 6 was produced in accordance with the following production method.

In an argon atmosphere, a mixture of t-butyl alcohol (39 g), 91 g of a fluoropolyether represented by HO—CH$_2$CF$_2$O(CF$_2$CF$_2$O)$_x$(CF$_2$O)$_y$CF$_2$CH$_2$—OH (the number average molecular weight: 2:393, the molecular weight distribution: 1.32), potassium t-butoxide (0.7 g), and glycidol (10 g) was stirred at 70° C. for 14 hours. The mixture was then washed with water, dehydrated, and purified by silica gel column chromatography, thereby giving 82 g of compound 6 having two hydroxyl groups at each terminal (the average molecular weight: 2432).

Compound 6 was a colorless transparent liquid, and had a density of 1.73 g/cm$^3$ at 20° C. Compound 6 was identified by NMR as shown below.

$^{19}$F-NMR (solvent: none, standard substance: OCF$_2$C$\underline{F}_2$CF$_2$CF$_2$O in the obtained product, which was taken as −125.8 ppm)

δ=−52.1 ppm, −53.7 ppm, −55.4 ppm

[24F, —OC$\underline{F}_2$O—],

δ=−89.1 ppm, −90.7 ppm

[48F, —OC$\underline{F}_2$C$\underline{F}_2$O—],

δ=−77.9 ppm, −80.0 ppm

[4F, —OC$\underline{F}_2$CH$_2$OCH$_2$CH(OH)CH$_2$OH], x=12.1, y=12.3

$^1$H-NMR (solvent: none, standard substance: D$_2$O)

δ=3.2 to 3.8 ppm

[18H, HOC$\underline{H}_2$C$\underline{H}$(O$\underline{H}$)C$\underline{H}_2$OC$\underline{H}_2$—CF$_2$O(CF$_2$CF$_2$O)$_x$(CF$_2$O)$_y$CF$_2$C$\underline{H}_2$—O—C$\underline{H}_2$C$\underline{H}$(O$\underline{H}$)C$\underline{H}_2$O$\underline{H}$]

Compound 7 is a compound represented by formula (5) (HOCH$_2$CH(OH)CH$_2$OCH$_2$CF$_2$CF$_2$O(CF$_2$CF$_2$CF$_2$O)$_n$CF$_2$CF$_2$CH$_2$OCH$_2$OH(OH)CH$_2$OH) disclosed in paragraph [0004] of Patent Literature 2 (WO2009/066784).

Compound 7 was produced in accordance with the following production method, and had two hydroxyl groups at each terminal of the molecule.

In an argon atmosphere, a mixture of t-butyl alcohol (41 g), 95 g of a fluoropolyether represented by HO—$CH_2CF_2CF_2O(CF_2CF_2CF_2O)_nCF_2CF_2CH_2$—OH (the number average molecular weight: 1850, the molecular weight distribution: 1.25), potassium t-butoxide (0.8 g), and glycidol (11 g) was stirred at 70° C. for 14 hours. The mixture was then washed with water, dehydrated, and purified by silica gel column chromatography, thereby giving 90 g of compound 7 having two hydroxyl groups at each terminal (the average molecular weight: 1936).

Compound 7 was a colorless transparent liquid, and had a density of 1.75 g/cm$^3$ at 20° C. Compound 7 was identified by NMR as shown below.

$^{19}$F-NMR (solvent: none, standard substance: $OCF_2C\underline{F}_2CF_2O$ in the obtained product, which was taken as −129.7 ppm)
  δ=−129.7 ppm
  [26F, —$OCF_2C\underline{F}_2CF_2O$—],
  δ=−83.7
  [52F, —$OC\underline{F}_2CF_2C\underline{F}_2O$—],
  δ=−124.2 ppm
  [4F, —$OC\underline{F}_2CF_2CH_2OCH_2CH(OH)CH_2OH$],
  δ=−86.5 ppm.
  [4F, —$OCF_2C\underline{F}_2CH_2OCH_2CH(OH)CH_2OH$]
  n=13.0
$^1$H-NMR (solvent: none, standard substance: $D_2O$)
  δ=3.2 to 3.8 ppm
  [18H, $\underline{H}O$—$CH_2C\underline{H}(O\underline{H})C\underline{H}_2O$—$C\underline{H}_2CF_2CF_2O$ $(CF_2CF_2CF_2O)_nCF_2CF_2C\underline{H}_2$—$O$—$C\underline{H}_2C\underline{H}(O\underline{H})C\underline{H}_2O\underline{H}$]

Test Example 1: Measurement of Bonding Rate

Each compound was dissolved in Vertrel-XF, product of DuPont, to prepare a lubricant. A magnetic disk, 2.5 inches in diameter, was immersed in the solution for 1 minute and then withdrawn at a rate of 2 mm/s. The disk coated with the lubricant was then inserted into an ultraviolet irradiator equipped with a low-pressure mercury lamp that emits ultraviolet rays at a wavelength of 185 nm and 254 nm, and maintained for 10 to 20 seconds. To prevent ozone formation, the inside of the ultraviolet irradiator had been replaced with nitrogen beforehand. The average film thickness of the compound on the disk was then measured by a Fourier Transform Infrared Spectrometer (FT-IR). This film thickness was taken as fÅ. Subsequently, the disk was immersed in a mixed solvent of Vertrel-XF and methanol (a volume ratio of 70:30) for 5 minutes, withdrawn at a rate of 2 mm/s, and allowed to stand at room temperature for volatilization of the solvent. The average film thickness of the compound remaining on the disk was measured with FT-IR, and the film, thickness was taken as bÅ. The bonding rate, which is typically used, was used as an indicator to show the degree of adsorption of the lubricant to the disk. The bonding rate is expressed by the following equation.

$$\text{Bonding Rate (\%)} = 100 \times b/f$$

TABLE 1

|  | Compound 1 | Compound 2 | Compound 3 | Compound 4 | Compound 5 | Compound 6 | Compound 7 |
|---|---|---|---|---|---|---|---|
| Bonding Rate (%) | 48 | 50 | 46 | 48 | 36 | 35 | 29 |

Table 1 shows that compounds 1 to 4 of the present in have higher bonding rates than compounds 5 to 7, which are Comparative Examples.

Test Example 2: Evaluation of Decomposition Using Ultraviolet Irradiator and Thermal Analyzer (TG/TDA)

0.3 g of each compound was individually placed in a Petri dish, and irradiated with an ultraviolet irradiator (wavelength 185 nm and 254 nm) in a nitrogen atmosphere for 6 hours. Compounds 1 to 7 before ultraviolet irradiation and compounds 1 to 7 after ultraviolet irradiation were heated at a temperature increase rate of 2° C./min in a nitrogen atmosphere, and the temperature at which the weight of each compound decreased by 10% was measured with a thermal analyzer (TG/TDA). The samples before ultraviolet irradiation and the samples after ultraviolet irradiation were compared in terms of the temperatures at which they lost their 10% weight to evaluate the decomposition of the compounds.

TABLE 2

|  | Compound 1 | Compound 2 | Compound 3 | Compound 4 | Compound 5 | Compound 6 | Compound 7 |
|---|---|---|---|---|---|---|---|
| Before UV Irradiation (° C.) | 297 | 305 | 279 | 294 | 294 | 234 | 280 |
| After UV Irradiation (° C.) | 253 | 260 | 256 | 252 | 292 | 236 | 275 |

Table 2 shows that whereas the temperature at which weight decrease occurred did not change before and after ultraviolet irradiation in the case of compounds 5 to 7 (i.e., Comparative Examples), the lubricants of compounds 1 to 4 of the present invention exposed to ultraviolet irradiation decomposed and scattered at temperatures lower than the temperatures at which compounds 1 to 4 decomposed before exposure to ultraviolet irradiation. This indicates that ultraviolet irradiation to compounds 1 to 4 of the present invention cleaved the bonds between the carbon atoms of the $C_{4-10}$ aliphatic hydrocarbon chain present in the middle of the molecule and the oxygen atoms to thereby generate compounds having a lower molecular weight, which evaporated at a lower temperature than before ultraviolet irradiation. Compounds 5 to 7, however, do not contain a $C_{4-10}$ aliphatic hydrocarbon chain in the middle of the molecule, and such cleavage of ether linkage did not occur under ultraviolet irradiation, thus resulting in substantially no change in temperature at which the weight of the compound decreased between before and after ultraviolet irradiation.

The results suggest that the compound of the present invention containing a $C_{4-10}$ aliphatic hydrocarbon chain in the middle of the molecule is cleaved between the carbon atoms of the $C_{4-10}$ aliphatic hydrocarbon chain and the oxygen atoms by ultraviolet irradiation, and the portions where ether linkages are cleaved bind to the surface of the magnetic disk, enhancing the bonding rate.

DESCRIPTION OF THE REFERENCE NUMERALS 1 substrate
2 recording layer
3 protective layer
4 lubricant layer

The invention claimed is:

1. A fluoropolyether compound comprising
   (i) a $C_{4-10}$ aliphatic hydrocarbon chain present in the middle of the fluoropolyether compound and
   (ii) at least two perfluoropolyethers, each perfluoropolyether being ether-linked to the $C_{4-10}$ aliphatic hydrocarbon chain,
   the $C_{4-10}$ aliphatic hydrocarbon chain having at least one hydroxyl group,
   the at least two perfluoropolyethers having, at respective non-hydrocarbon chain terminals, at least one polar group selected from the group consisting of —OH, —OCH$_2$CH(OH)CH$_2$OH, —OCH$_2$CH(OH)CH$_2$OCH$_2$CH(OH)CH$_2$OH, —O(CH$_2$)$_m$OH, and —OCH$_2$(OH)CHCH$_2$—OC$_6$H$_4$—R$^1$,
   wherein m is an integer of 2 to 8, and R$^1$ represents hydrogen, C$_{1-4}$ alkoxy, amino, or an amide residue.

2. The fluoropolyether compound according to claim 1, wherein the $C_{4-10}$ aliphatic hydrocarbon chain has 8 carbon atoms.

3. The fluoropolyether compound according to claim 1, which is at least one member selected from the group consisting of
   HOCH$_2$CH(OH)CH$_2$OCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OCH$_2$CH(OH)CH$_2$OH, wherein z is a real number of 0 to 30,
   HOCH$_2$CH(OH)CH$_2$OCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OCH$_2$CH(OH)CH$_2$OH, wherein w is a real number of 0 to 20,
   HOCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OH, wherein z is a real number of 0 to 30, and
   HOCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OH, wherein w is a real number of 0 to 20.

4. A lubricant comprising the fluoropolyether compound according to claim 1.

5. A magnetic disk comprising, in sequence over a substrate: a recording layer, a protective layer, and a lubricant layer,
   wherein the lubricant layer is formed by applying the lubricant according to claim 4 to the surface of the protective layer, and performing ultraviolet irradiation or heat treatment.

6. A method for producing a magnetic disk that comprises in sequence over a substrate, a recording layer, a protective layer, and a lubricant layer, the method comprising
   forming the recording layer and the protective layer over the substrate in this order,
   applying the lubricant according to claim 4 to the surface of the protective layer, and
   performing ultraviolet irradiation or heat treatment to form the lubricant layer.

7. The fluoropolyether compound according to claim 2, which is at least one member selected from the group consisting of
   HOCH$_2$CH(OH)CH$_2$OCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OCH$_2$CH(OH)CH$_2$OH, wherein z is a real number of 0 to 30,
   HOCH$_2$CH(OH)CH$_2$OCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OCH$_2$CH(OH)CH$_2$OH wherein w is a real number of 0 to 20,
   HOCH$_2$CF$_2$CF$_2$O(CF$_2$CF$_2$CF$_2$O)$_z$CF$_2$CF$_2$CH$_2$—OCH$_2$CH(OH)CH$_2$CH$_2$CH$_2$CH$_2$CH(OH)CH$_2$O—CH$_2$CF$_2$CF$_2$O(CF$_2$CF$_2$CF$_2$O)$_z$CF$_2$CF$_2$CH$_2$OH, wherein z is a real number of 0 to 30, and
   HOCH$_2$CF$_2$CF$_2$CF$_2$O(CF$_2$CF$_2$CF$_2$CF$_2$O)$_w$CF$_2$CF$_2$CF$_2$CH$_2$—OCH$_2$CH(OH)CH$_2$CH$_2$CH$_2$CH$_2$CH(OH)CH$_2$O—CH$_2$CF$_2$CF$_2$CF$_2$O(CF$_2$CF$_2$CF$_2$CF$_2$O)$_w$CF$_2$CF$_2$CF$_2$CH$_2$OH, wherein w is a real number of 0 to 20.

8. A lubricant comprising the fluoropolyether compound according to claim 2.

9. The fluoropolyether compound according to claim 1, wherein the at least two perfluoropolyethers comprises, at respective non-hydrocarbon chain terminals, —OH, —OCH$_2$CH(OH)CH$_2$OH.

10. The fluoropolyether compound according to claim 1, wherein the at least two perfluoropolyethers comprises, at respective non-hydrocarbon chain terminals, —OCH$_2$CH(OH)CH$_2$OCH$_2$CH(OH)CH$_2$OH.

11. The fluoropolyether compound according to claim 1, wherein the at least two perfluoropolyethers comprises, at respective non-hydrocarbon chain terminals, —O(CH$_2$)$_m$OH, and —OCH$_2$(OH)CHCH$_2$—OC$_6$H$_4$—R$^1$.

12. The fluoropolyether compound according to claim 1, wherein R$^1$ is hydrogen.

13. The fluoropolyether compound according to claim 1, wherein R$^1$ is C$_{1-4}$ alkoxy.

14. The fluoropolyether compound according to claim 1, wherein R$^1$ is amino.

15. The fluoropolyether compound according to claim 1, wherein R$^1$ is an amide residue.

16. The fluoropolyether compound according to claim 3, wherein z is not 0, and w is not 0.

17. The fluoropolyether compound according to claim 3, wherein z is a real number of 2 to 8, and w is a real number of 1 to 5.

* * * * *